US 6,699,868 B2

(12) United States Patent
Pystynen et al.

(10) Patent No.: US 6,699,868 B2
(45) Date of Patent: Mar. 2, 2004

(54) PYRIDAZINYL PHENYL HYDRAZONES USEFUL AGAINST CONGESTIVE HEART FAILURE

(75) Inventors: Jarmo Pystynen, Espoo (FI); Aino Pippuri, Espoo (FI); Anne Luiro, Helsinki (FI); Pentti Nore, Helsinki (FI); Reijo Bäckström, Helsinki (FI); Kari Lönnberg, Turku (FI); Heimo Haikala, Espoo (FI); Jouko Levijoki, Helsinki (FI); Petri Kaheinen, Helsinki (FI); Juha Kaivola, Helsinki (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 10/221,348
(22) PCT Filed: Mar. 12, 2001
(86) PCT No.: PCT/FI01/00241
§ 371 (c)(1),
(2), (4) Date: Dec. 26, 2002
(87) PCT Pub. No.: WO01/68611
PCT Pub. Date: Sep. 20, 2001

(65) Prior Publication Data
US 2003/0158200 A1 Aug. 21, 2003

(30) Foreign Application Priority Data
Mar. 13, 2000 (FI) .............................. 20000577

(51) Int. Cl.⁷ ...................... A61K 31/50; A61K 31/502; C07D 237/04; C07D 237/26; C07D 237/32
(52) U.S. Cl. ...................... 514/247; 514/248; 544/235; 544/237; 544/239
(58) Field of Search ................................ 544/237, 239, 544/235; 514/247, 248

(56) References Cited

U.S. PATENT DOCUMENTS

| | | | |
|---|---|---|---|
| 4,851,406 A | | 7/1989 | Mertens et al. .............. 514/212 |
| 5,019,575 A | * | 5/1991 | Haikala et al. .............. 514/247 |
| 5,122,524 A | * | 6/1992 | Haikala et al. .............. 514/242 |
| 5,185,332 A | * | 2/1993 | Haikala et al. .......... 514/222.5 |

FOREIGN PATENT DOCUMENTS

| | | |
|---|---|---|
| EP | 0 383 449 | 8/1990 |
| EP | 0 223 937 | 6/1997 |
| GB | 2 228 004 | 8/1990 |

OTHER PUBLICATIONS

Mertens et al., "Nonsteroidal Cardiotonics. 3. New 4,5–Dihydro–6–(1H–indol–5–yl)pyridazine–3(2H)–ones and Related Compounds with Positive Inotropic Activities," J. Med. Chem. vol. 33, pp. 2870–2875 (1990).

* cited by examiner

Primary Examiner—Emily Bernhardt
(74) Attorney, Agent, or Firm—Finnegan, Henderson, Farabow, Garrett & Dunner, LLP

(57) ABSTRACT

Therapeutically active compounds of formula (I):

(I)

in which $R_1$ to $R_4$ means hydrogen, alkyl, alkenyl, aryl, arylalkyl, carboxyalkyl, hydroxyalkyl or halogenalkyl, or $R_2$ and $R_3$ form a ring of 5–7 carbon atoms, $R_5$ to $R_9$ means hydrogen, alkyl, alkenyl, aryl, arylalkyl, acyl, hydroxy, alkoxy, alkoxycarbonyl, amino, acylamino, alkylamino, aryloxy, halogen, cyano, nitro, carboxy, alkylsufonyl, sulfonamido or trifluoromethyl, wherein each aryl residue defined above by itself or as a part of another group may be substituted, and pharmaceutically acceptable salts and esters thereof. The compounds increase the calcium sensitivity of contractile proteins of the cardiac muscle and are thus useful in the treatment of congestive heart failure.

11 Claims, No Drawings

PYRIDAZINYL PHENYL HYDRAZONES USEFUL AGAINST CONGESTIVE HEART FAILURE

This application is a national stage filing of PCT International Application No. PCT/FI01/00241, filed on Mar. 12, 2001. This application also claims the benefit of priority under 35 U.S.C. § 119(a) to Finnish patent application No. 20000577, filed on Mar. 13, 2000.

The present invention relates to pyridazinyl phenyl hydrazone compounds and pharmaceutically acceptable salts and esters thereof. The invention also relates to pharmaceutical compositions comprising such compounds as active ingredients. The compounds of the invention increase the calcium sensitivity of contractile proteins of the cardiac muscle and are thus useful in the treatment of congestive heart failure.

Congestive heart failure is characterized by a decrease in cardiac output and an increase in right and left ventricular filling pressure. These hemodynamic conditions can produce symptoms of dyspnea, fatigue and edema.

The contraction in cardiac muscle is triggered by the binding of calcium to contractile proteins. Series of phosphodiesterase isoenzyme III (PDE III) inhibitors are in clinical trials for the treatment of congestive heart failure. These compounds increase the contractility of the cardiac muscle and produce vasodilatation. However, it is known that the long-term application of those compounds may lead to calcium overload in the cardiac muscle and trigger arrhythmias. It is therefore desired to develop medicaments acting by a mechanism which would increase cardiac contractility without producing calcium overload. The increase of calcium sensitivity of contractile proteins would be such a mechanism.

Pyridazinyl phenyl hydrazone compounds have been described earlier in European patent application EP 383449. The compounds show calcium dependent binding to contractile proteins of the cardiac muscle, as well as PDE III inhibiting activity. In the specific examples one 1-acetyl-1-phenyl methylidene derivative is disclosed (Ex. 16). While the 1-acetyl-1-phenyl methylidene derivative has some effect in cardiac contractility, it does not increase the calcium sensitivity of contractile proteins.

Certain pyridazinyl phenyl hydrazone compounds appear as intermediates in European patent applications EP 223937 and EP 280224. However, the compounds are not specifically characterized. Mertens, A. et al., J. Med. Chem. 1990, 33, 2870-2875,discloses a phenyl, 4-methoxyphenyl and 2-hydroxyphenyl derivatives of pyridazinyl phenyl hydrazone compounds as intermediates.

It has now been found that compounds of formula (I) are potent in increasing the calcium sensitivity of contractile proteins in the cardiac muscle:

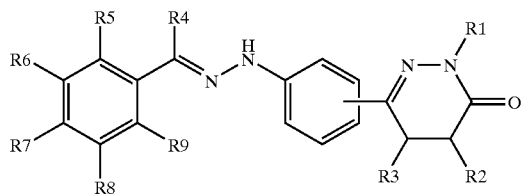

(I)

in which $R_1$ to $R_4$ means hydrogen, alkyl, alkenyl, aryl, arylalkyl, carboxyalkyl, hydroxyalkyl or halogenalkyl, or $R_2$ and $R_3$ form a ring of 5–7 carbon atoms, $R_5$ to $R_9$ means hydrogen, alkyl, alkenyl, aryl, arylalkyl, acyl, hydroxy, alkoxy, alkoxycarbonyl, amino, acylamino, alkylamino, aryloxy, halogen, cyano, nitro, carboxy, alkylsulfonyl, sulfonamido or trifluoromethyl, wherein each aryl residue defined above by itself or as a part of another group may be substituted, and pharmaceutically acceptable salts and esters thereof, provided that a) when $R_1$, $R_2$, $R_3$, $R_5$, $R_6$, $R_8$ and $R_9$ are hydrogen and $R_4$ is methyl, $R_7$ is not hydrogen or methoxy and b) when $R_1$, $R_2$, $R_3$, $R_5$, $R_6$, $R_7$ and $R_8$ are hydrogen and $R_4$ is methyl, $R_9$ is not hydroxy.

The invention also relates to compounds of formula (I) in which $R_1$, $R_2$, $R_3$, $R_5$, $R_6$, $R_8$ and $R_9$ are hydrogen, $R_4$ is methyl, and $R_7$ is hydrogen or methoxy, or in which $R_1$, $R_2$, $R_3$, $R_5$, $R_6$, $R_7$ and $R_8$ are hydrogen, $R_4$ is methyl and $R_9$ is hydroxy and pharmaceutically acceptable salts and esters thereof, for use as a medicament.

In a class of preferred compounds and pharmaceutically acceptable salts and esters are compounds of formula (I) wherein $R_5$ to $R_9$ are independently hydrogen, $C_{1-6}$alkyl, $C_{1-6}$alkenyl, $C_{6-10}$aryl, $C_{7-12}$arylalkyl, $C_{1-6}$acyl, hydroxy, $C_{1-6}$alkoxy, $C_{1-6}$alkoxycarbonyl, amino, $C_{1-6}$acylamino, $C_{1-6}$alkylamino, $C_{6-10}$aryloxy, halogen, cyano, nitro, carboxy, $C_{1-6}$alkylsulfonyl, sulfonamido or trifluoromethyl. In a subclass of this class of compounds and pharmaceutically acceptable salts thereof are compounds of formula (I) wherein $R_5$ to $R_9$ are independently hydrogen, hydroxy, $C_{1-6}$alkyl, $C_{1-6}$alkoxy, carboxy, $C_{1-6}$alkoxycarbonyl or nitro. In a subclass of this class of compounds and pharmaceutically acceptable salts thereof are compounds of formula (I) wherein $R_5$ is hydroxy, $C_{1-6}$alkyl, $C_{1-6}$alkoxy, carboxy, $C_{1-6}$alkoxycarbonyl or nitro, most preferably hydroxy or nitro.

In another class of preferred compounds and pharmaceutically acceptable salts $R_1$ to $R_4$ are independently hydrogen, $C_{1-6}$alkyl, $C_{1-6}$alkenyl, $C_{6-10}$aryl, $C_{7-12}$arylalkyl, $C_{1-6}$carboxyalkyl, $C_{1-6}$hydroxyalkyl or $C_{1-6}$halogenalkyl, or $R_2$ and $R_3$ form a phenyl ring. In a subclass of this class of compounds and pharmaceutically acceptable salts thereof are compounds of formula (I) wherein $R_1$ to $R_3$ are independently hydrogen or $C_{1-6}$alkyl.

Each aryl residue in each of these preferred classes of compounds, by itself or as part of another group, may be substituted by 1 to 3, preferably 1 or 2, of fluorine, chlorine, bromine, iodine, hydroxy, nitro, carboxy, trifluoromethyl, amino, $C_{1-4}$alkyl, $C_{1-4}$alkoxy, $C_{1-6}$acyl, $C_{1-6}$carboxyalkyl, phenyl, naphthyl, halophenyl, halonaphthyl, benzyl, phenethyl, halobenzyl, halophenethyl, naphthylmethyl, naphthylethyl, $C_{4-7}$cycloalkyl, $C_{1-4}$alkyl $C_{4-7}$cycloalkyl, mono $C_{1-4}$alkylamino, di $C_{1-4}$alkylamino, $C_{1-6}$alkanoylamino, phenylcarbonylamino, naphthylcarbonylamino, cyano, thiol, or $C_{1-6}$alkylthio.

The compounds of formula (I) may contain one or more assymmetric centers and thus they can exist as enantiomers or diastereomers. The invention includes both mixtures and separate individual isomers.

Especially preferred individual compounds of the invention include:

(R)-6-{4-[N'-(4-Hydroxy-3-methoxy-2-nitro-benzylidene)-hydrazino]-phenyl }-5-methyl-4,5-dihydro-2H-pyridazin-3-one;

6-{4-[N'-(4-Hydroxy-3-methoxy-2-nitro-benzylidene)-hydrazino]-phenyl}-5-methyl-4,5-dihydro-2H-pyridazin-3-one;

6-(4-{N'-[1-(2,5-Dihydroxy-phenyl)-ethylidene]-hydrazino}-phenyl)-5-methyl-4,5-dihydro-2H-pyridazin-3-one;

6-(4-{N-[1-(2,4-Dihydroxy-3-methylphenyl)ethylidene]
hydrazino}phenyl)-5-methyl-4,5-dihydro-2H-pyridazin-
3-one;
6-(4-{N'-[Bis-(2,4-dihydroxy-phenyl)-methylene]-
hydrazino}-phenyl)-5-methyl-4,5-dihydro-2H-pyridazin-
3-one;
6-(4-{N'-[1-(2,4-Dihydroxy-phenyl)-ethylidene]-
hydrazino}-phenyl)-5-methyl-4,5-dihydro-2H-pyridazin-
3-one;
2,6-Dihydroxy-3-{[4-(4-methyl-6-oxo-1,4,5,6-tetrahydro-
pyridazin-3-yl)-phenyl]-hydrazonomethyl }-benzoic acid
ethyl ester; and
6-{4-[N'-(3-Ethyl-2,4-dihydroxy-benzylidene)-hydrazino]-
phenyl}-5-methyl-4,5-dihydro-2H-pyridazin-3-one.

The compounds of the invention can be prepared by the well known condensation reaction between a carbonyl compound and a hydrazine as shown in Scheme 1:

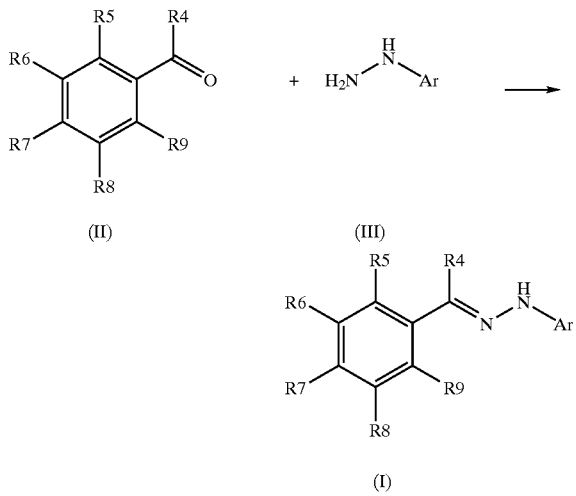

wherein Ar means

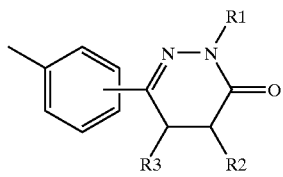

and $R_1$ to $R_9$ as defined above.

A suitable method for the preparation of hydrazines (III) is the diazotization of an aniline and reduction as a one pot synthesis. Scheme 2 shows this reaction:

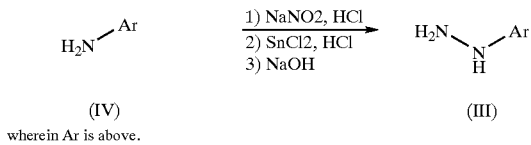

where Ar is as above.

Compounds of formula (II) and (IV) are commercially available or can be prepared using methods known in the literature.

General method 1: In case where $R_4$ is hydrogen, the reaction of Scheme 1 is generally performed by refluxing a mixture of compounds (II) and (III) in a suitable solvent, such as ethanol, 2-propanol, acetonitrile or acetic acid, for 1–24 hours. The product (I) is filtered.

General method 2: In case where $R_4$ is not hydrogen, the reaction of Scheme 1 is generally performed by heating a neat mixture of compounds (II) and (III) at 140–170° C. under inert atmosphere. The mixture is then triturated with ethyl acetate and the product (I) filtered.

Salts and esters of the compounds, when applicable, may be prepared by known methods. Physiologically acceptable salts are useful as active medicaments, however, preferred are the salts with alkali or alkaline earth metals. Physiologically acceptable esters are also useful as active medicaments. Examples are the esters with aliphatic or aromatic alcohols.

The term "alkyl" as employed herein by itself or as part of another group includes both straight, branched and cyclized chain radicals of up to 18 carbon atoms, preferably 1 to 8 carbon atoms, most preferably 1 to 4 carbon atoms. The term "lower alkyl" as employed herein by itself or as part of another group includes straight, branched and cyclized chain radicals of 1 to 7,preferably 1 to 4,most preferably 1 or 2 carbon atoms. Specific examples for the alkyl and lower alkyl residues, respectively, are methyl, ethyl, propyl, isopropyl, butyl, tert. butyl, pentyl, cyclopentyl, hexyl, cyclohexyl, octyl, decyl and dodecyl including the various branched chain isomers thereof.

The term "acyl" as employed herein by itself or as part of another group refers to an alkylcarbonyl or alkenylcarbonyl group, the alkyl and alkenyl groups being defined above.

The term "aryl" as used herein by itself or as part of another group refers to a monocyclic or bicyclic group containing from 6 to 10 carbon atoms in the ring portion. Specific examples for aryl groups are phenyl, naphtyl and the like. "Aroyl" means in a corresponding way an arylcarbonyl group.

The term "alkoxy" as employed herein by itself or as part of another group includes an alkyl group as defined above linked to an oxygen atom. "Aryloxy" means in a corresponding way an aryl group linked to an oxygen atom.

The term "substituted" as used herein in connection with various residues refers to halogen substituents, such as fluorine, chlorine, bromine, iodine or trifluoromethyl group, amino, alkyl, alkoxy, aryl, alkyl-aryl, halogen-aryl, cycloalkyl, alkylcycloalkyl, hydroxy, alkylamino, alkanoylamino, arylcarbonylamino, nitro, cyano, thiol, or alkylthio substituents.

The "substituted" groups may contain 1 to 3,preferably 1 or 2 of the above mentioned substituents.

Compounds of the invention may be administered to a patient in therapeutically effective amounts which range usually from about 0.1 to 500 mg per day depending on the age, weight, condition of the patient, administration route and the phospholamban inhibitor used. The compounds of the invention can be formulated into dosage forms using the principles known in the art. It can be given to a patient as such or in combination with suitable pharmaceutical excipients in the form of tablets, dragees, capsules, suppositories, emulsions, suspensions or solutions. Choosing suitable ingredients for the composition is a routine for those of ordinary skill in the art. It is evident that suitable carriers, solvents, gel forming ingredients, dispersion forming ingredients, antioxidants, colours, sweeteners, wetting compounds and other ingredients normally used in this field of technology may be also used. The compositions containing the active compound can be given enterally or parenterally, the oral route being the preferred way. The contents of the active compound in the composition is from about 0.5 to 100%, preferably from about 0.5 to about 20%, per weight of the total composition.

The usefulness of the compounds of the invention is demonstrated by the following experiments.

Experiment 1. Calcium sensitizing effect in skinned cardiac fiber

Method

The heart of a guinea-pig was excised and perfused with ice-cold saponin (125 mg/l) skinning solution consisting of (mM): $K^+$-acetate 74.7. EGTA-$Na_2$ 10, $MgSO_4$ 5.4, ATP-$Na_2$ 4, MOPS 20, pH 7.0 (by 1 M KOH). Left ventricular papillary muscle was dissected and sonicated at 10 Watt for 60 s. The distance between ultrasound probe and the papillary muscle was 10 mm. The fibres (<200 µm in diameter) were dissected from the surface of sonicated papillary muscles in the same solution.

The fibre was glued between platinum wires, one attached to an isometric force transducer (type AE-801,SensoNor, Horten, Norway) and another to a micro manipulator. The fibre was relaxed in a solution consisting of (mM): EGTA-$Na_2$ 10, $MgSO_4$ 5.4, ATP-$Na_2$ 4, MOPS 20. The pH of the solution was adjusted to 7.0 and ionic strength to 0.16 M by the addition of KOH and $K^+$-acetate. Creatine kinase and creatine phosphate were not added as an ATP generating system because the developed tension was well sustained for the time required for experiment. The calculations for ionic strength and for free calcium (pCa 7.0–6.2) were performed using a suitable program. The fibres were stretched in relaxing solution until resting tension was just noticeable. When the calcium (pCa 6.0 or 6.2)-induced tension had reached steady state the test compound (final concentrations 0.1, 0.3, 1, 3,and 10 µM) was cumulatively added into the solution at 6 min intervals. All the experiments were carried out with fresh fibres at normal room temperature.

Results

The calcium sensitizing effect of the compounds are shown in Table 1.

TABLE 1

Maximum calcium sensitizing effect in skinned fiber (change in force, % change from control). The Reference compound is Ex. 16 of EP 383449.

| Compound of Example No. | Change in force/ % change from control |
|---|---|
| 2 | 207.2 |
| 6 | 32.9 |
| 21 | 44.2 |
| 23 | 39.9 |
| 24 | 42.0 |
| 33 | 55.2 |
| 34 | 52.8 |
| 35 | 25.4 |
| 37 | 21.7 |
| 38 | 32.2 |
| 40 | 100.2 |
| 43 | 39.0 |
| 49 | 28.7 |
| Ref. compound | No effect |

Experiment 2. Effect in left ventricular pressure derivatives in isolated heart

After sacrification the heart of a guinea-pig was rapidly excised and rinsed in oxygenated perfusion buffer. A cannula was inserted into the aorta and secured with a ligature. Retrograde perfusion began as soon as the heart was placed in a thermostatically controlled moist chamber of the Langendorff apparatus (Hugo Sachs Elektronik, KG). Modified Tyrode solution (37° C.), equilibrated in a thermostatically controlled bulb oxygenator with carbogen (95% $O_2$ and 5% $CO_2$), was used as a perfusion buffer. The composition of the Tyrode solution was (in mM): NaCl 135; $MgCl_2 \times 6H_2O$ 1; KCl 5; $CaCl_2 \times 2H_2O$ 2; $NaHCO_3$ 15; $Na_2HPO_4 \times 2H_2O$ 1; glucose 10; pH 7.3–7.4. The perfusion buffer was delivered at the top of the oxygenator by a pump and driven automatically by its controller. Subsequently, the buffer was delivered into the bulbs of the oxygenator chamber by a rotating disk. It was dispersed by making a thin fluid film on a large inner oxygenator surface in $O_2/CO_2$ atmosphere leading to saturation of the perfusate with oxygen (partial pressure 660 mmHg at 37° C.).

The experiments were carried out under constant pressure condition (50 mmHg). After a short prestabilization (10 min) a latex balloon (size 4) was carefully placed into the left ventricle through the left pulmonary vein and the left atrium. The latex balloon was attached to a stainless-steel cannula coupled with a pressure transducer. The latex balloon, the cannula and the chamber of the pressure transducer were carefully filled with ethylene glycol/water (1:1) mixture avoiding any air-bubble. The isovolumetric left ventricular pressure was recorded through the pressure transducer. At the beginning of the experiment, the volume of the balloon was adjusted to obtain a diastolic pressure of approximately 5 mmHg. Before starting the experiment the heart was allowed to stabilise further for 30–50 min. The systolic and end-diastolic left ventricular pressures were recorded for calculating the maximal positive and negative derivatives of the left ventricular pressure.

Results

The $EC_{50}$ values (µM) of various compounds of the invention on maximal positive derivative of the left ventricular systolic pressure are shown in Table 2.

| Compound of Example No. | $EC_{50}$ (µM) |
|---|---|
| 2 | 0.02 |
| 6 | 0.31 |
| 21 | 3.04 |
| 23 | 2.47 |
| 33 | 0.4 |
| 34 | 0.11 |
| 35 | 0.31 |
| 40 | 0.71 |
| 43 | 1.75 |
| 49 | 0.25 |

To further illustrate the invention, but not by way of limitation, the following examples are provided. The melting points were determined on a Reichert plate melting point apparatus and were not corrected. NMR-spectra were recorded on using a Bruker ARX 400 spectrometer with internal TMS as the reference (0 ppm).

EXAMPLES

Example 1 (Intermediate Compound)

(R)-6-(4-hydrazino-phenyl)-5-methyl-4,5-dihydro-2H-pyridazin-3-one

A slight modification on the procedure described in J.Med.Chem. (1990), 33(10), 2870–2875 was used as follows. A solution of sodium nitrite (1.7 g) in water (12.5 ml) was added slowly at 0–5° C. to a solution of (R)-6-(4-aminophenyl)-5-methyl-4,5-dihydro-2H-pyridazin-3-one (5 g) in 1 M hydrochloric acid (75 ml). The resulting solution was stirred on ice bath for five minutes and then added slowly to a solution of tin(II)chloride dihydrate (17 g) in 1 M hydrochloric acid (150 ml) keeping the reaction temperature below 5° C. This solution was stirred on ice for forty minutes and then a solution of 50% NaOH (75 ml) was quickly added. The resulting mixture was stirred on ice bath until the temperature reached zero degrees Celsius. The crystals were filtered and washed with dilute ammonia. Yield: 5.0 g, 93%.

HPLC: enantiomerically pure.

$^1$H NMR (400 MHz, DMSO-$d_6$): δ=1.04 (d, 3H, $CH_3$), 2.17 (d, 1H, J=16 Hz), 2.60 (m, 1H), 3.29 (m, 1H), 4.04 (s, 2H, $NH_2$), 6.77 (d, 2H, J=8 Hz), 7.09 (b, 1H, NH), 7.54 (d, 2H, J=8 Hz), 10.66 (s, 1H, NHCO).

Example 2

(R)-6-{4-[N'-(4-Hydroxy-3-methoxy-2-nitro-benzylidene)-hydrazino]-phenyl }-5-methyl-4,5-dihydro-2H-pyridazin-3-one A solution of 4-hydroxy-3-methoxy-2-nitro-benzaldehyde (1.6 g) in ethanol (15 ml) was added to a suspension of (R)-6-(4-hydrazino-phenyl)-5-methyl-4,5-dihydro-2H-pyridazin-3-one (1.75 g) in ethanol (20 ml) and the resulting mixture refluxed for two hours. The resulting crystals were filtered at room temperature and washed with ethanol. Yield 2.37 g. HPLC: purity 99.4%, optical purity 99.8%.

$^1$H NMR (DMSO-$d_6$): δ=1.06 (d, 3H, $CH_3$), 2.18–2.22 (m, 1H), 2.64 (m, 1H), 3.34 (m, 1 H), 3.84 (s, 3H, $CH_3O$), 6.98 (d, 2H), 7.08 (d, 1H), 7.37 (d, 1H), 7.66 (d, 2H), 7.67 (s, 1H), 10.68 (s, 1H, NH), 10.77 (s, 1H, NHCO).

Further Examples

The following compounds were synthesized according to the General method 1 (as exemplified in the previous example) or according to the General method 2.

General Method 1:

Reflux a mixture of a hydrazine derivative (II) and a benzaldehyde derivative (III) in a suitable solvent (ethanol, 2-propanol, acetonitrile or acetic acid) for 1–24 hours. Filter the product.

General Method 2:

Heat a neat mixture of a hydrazine derivative (II) and a ketone (III) at 140–170° C. under inert atmosphere. Triturate with ethyl acetate and filter the product.

The following compounds are synthesized according to the general method 1 unless otherwise specified.

Example 3

2,6-Dihydroxy-3-{[4-(4-methyl-6-oxo-1,4,5,6-tetrahydro-pyridazin-3-yl)-phenyl]-hydrazonomethyl}-benzoic acid Ethyl Ester Yield 73%, Melting point: 203–208° C. $^1$H NMR (DMSO-$d_6$): δ=1.06 (d, 3H), 2.20–2.23 (m, 1H), 2.64–2.68 (m, 1H), 3.30–3.33 (m, 1H), 3.83 (s, 3H, $COOCH_3$), 6.49 (d, 1H), 6.93 (d, 2H), 7.40 (d, 1H), 7.69 (d, 2H), 8.09 (s, 1H), 10.40 (s, 1H), 10.57 (s, 1H), 10.76 (s, 1H), 11.54 (s 1H).

Example 4

6-{4-[N'-(2,4,5-trihydroxy-benzylidene)-hydrazinol]-phenyl}-5-methyl-4,5-dihydro-2H-pyridazin-3-one Yield: 82%, Melting point: 286–290° C. $^1$H NMR (DMSO-$d_6$): δ=1.06 (d, 3H), 2.18–2.22 (m, 1H), 2.61–2.67 (m, 1H), 3.30–3.35 (m, 1H), 6.32 (s 1H), 6.93–6.95 (m, 1H), 7.66 (d, 2H), 8.03 (s, 1H), 8.42 (s, 1H), 9.24 (s, 1H), 9.76 (s, 1H), 10.32 (s, 1H), 10.74 (s, 1H).

Example 5

6-{4-[N'-(2-Hydroxy-5-nitro-benzylidene)-hydrazino]-phenyl}-5-methyl-4,5-dihydro-2H-pyridazin-3-one Yield: 89%, Melting point: 299–300° C. $^1$H NMR (DMSO-$d_6$): δ=1.07 (d, 3H), 2.19–2.23 (m, 1H), 2.63–2.68 (m, 1H), 3.31–3.37 (m, 1H), 7.05–7.10 (m, 3H), 7.72 (d, 2H), 8.05–8.08 (m, 1H), 8.21 (s, 1H), 8.55–8.56 (m, 1H), 10.78 (s, 1H), 10.89 (s, 1H), 11.61 (s, 1H).

Example 6

6-{4-[N'-(4-Hydroxy-3-methoxy-2-nitro-benzylidene)-hydrazino]-phenyl}-5-methyl-4,5-dihydro-2H-pyridazin-3-one Yield: 87%, Melting point: 235–239° C. $^1$H NMR (DMSO-$d_6$): δ=1.06 (d, 3H), 2.18–2.22 (m, 1H), 2.62–2.68 (m, 1H), 3.31–3.34 (m, 1H), 3.84 (s, 3H, $CH_3O$), 6.98 (d, 2H), 7.08 (d, 1H), 7.37 (d, 1H), 7.65 (d, 2H), 7.67 (s, 1H), 10.67 (s, 1H), 10.76 (s, 1H).

Example 7

6-{4-[N'-(2,3-Dihydroxy-benzylidene)-hydrazino]-phenyl}-5-methyl-4,5-dihydro-2H-pyridazin-3-one Yield: 69%, Melting point: 245–247° C. $^1$H-NMR (DMSO-$d_6$): δ=1.06 (d, 3H), 2.19–2.23 (m 1H), 2.64–2.68 (m, 1H), 3.33–3.38 (m, 1H), 6.68–6.77 (m, 2H), 6.99–7.03 (m, 3H), 7.70 (d, 2H), 8.17 (s, 1H), 9.2 (b, 1H), 9.95 (s, 1H), 10.63 (s, 1H), 10.77 (s, 1H).

Example 8

6-{4-[N'-(2,5-Dihydroxy-benzylidene)-hydrazino]-phenyl}-5-methyl-4,5-dihydro-2H-pyridazin-3-one Yield: 89%, Melting point: 317–320° C. $^1$H-NMR (DMSO-$d_6$): δ=1.06 (d, 3H), 2.18–2.22 (m, 1H), 2.62–2.68 (m, 1H), 3.30–3.36 (m, 1H), 6.59–6.62 (m, 1H), 6.69–7.03 (m, 1H), 7.68 (d, 2H), 8.12 (s, 1H), 8.82 (s, 1H), 9.57 (s, 1H), 10.57 (s, 1H), 10.76 (s, 1H).

Example 9

6-{4-[N'-(3,4-Dihydroxy-2-nitro-benzylidene)-hydrazino]-phenyl}-5-methyl-4,5-dihydro-2H-pyridazin-3-one Yield: 70%, Melting point: 239–241° C. $^1$H-NMR (DMSO-$d_6$): δ=1.06 (d, 3H), 2.18–2.22 (m, 1H), 2.61–2.67 (m, 1H), 3.33–3.38 (m, 1H), 6.94–6.98 (m, 1H), 7.06 (d, 1H), 7.64–7.66 (m, 3H, ArH, CH=N), 9.94 (b, 1H), 10.48 (b, 1H), 10.59 (s, 1H), 10.75 (s, 1H).

Example 10

2-{[4-(4-Methyl-6-oxo-1,4,5,6-tetrahydro-pyridazin-3-yl)-phenyl]-hydrazonomethyl}-benzoic acid Yield: 61%, Melting point: 250–251° C. $^1$H-NMR (DMSO-$d_6$): δ=1.12 (d, 3H), 2.25–2.30 (m, 1H), 2.72–2.78 (m, 1H), 3.42–3.51 (m, 1H), 7.72 (d, 2H), 7.90–7.95 (m, 3H), 7.98–8.05 (m, 2H), 8.34–8.36 (m 1H), 8.61 (s, 1H), 11.03 (s, 1H).

Example 11

6-{4-[N'-(2-trifluoromethyl-benzylidene)-hydrazino]-phenyl}-5-methyl-4,5-dihydro-2H-pyridazin-3-one Yield: 62%, Melting point: 113–115° C. $^1$H-NMR (DMSO-d$_6$): δ=1.06 (d, 3H), 2.19–2.23 (m, 1H), 2.63–2.69 (m, 1H), 3.33–3.37 (m, 1H), 7.14 (d, 2H), 7.50–7.52 (m, 1H), 7.68–7.75 (m, 4H), 8.19–8.27 (m, 2H), 10.79 (s, 1H), 11.04 (s, 1H).

Example 12

Acetic acid 2-Methoxy-4-{[4-(4-methyl-6-oxo-1,4,5,6-tetrahydro-pyridazin-3-yl)-phenyl]-hydrazonomethyl}-3-nitro-phenyl ester Yield: 65%, Melting point: 220–223° C. $^1$H-NMR (DMSO-d$_6$): δ=1.07 (d, 3H), 2.18–2.23 (m, 1H), 2.38 (s, 3H, OCOCH$_3$), 2.62–2.67 (m, 1H), 3.33–3.38 (m, 1H), 3.85 (s, 3H), 7.03 (d, 2H), 7.46 (d, 1H), 7.60 (d, 1H), 7.72 (d, 2H), 7.75 (s, 1H), 10.79 (s, 1H), 10.98 (s, 1H).

Example 13

6-(4-{N'-[1-(3,5-Dihydroxy-phenyl)-ethylidene]-hydrazino}-phenyl)-5-methyl-4,5-dihydro-2H-pyridazin-3-one The title compound was prepared according to the general method 2.

Yield: 27%, melting point 162–166° C. $^1$H NMR (400 MHz, DMSO-d$_6$): δ=1.07 (d, 3H), 2.17 (s, 3H), 2.18–2.22 (m, 1H), 2.62–2.68 (m, 1H), 3.35–3.41 (m, 1H), 6.17 (s, 1H), 6.67 (s, 2H), 7.23 (d, 2H), 7.67 (d, 2H), 9.21 (s, 1H), 9.44 (s, 1H), 10.75 (s, 1H).

Example 14

6-(4-{N'-[1-(2,4-Dihydroxy-phenyl)-3-(3,4-dimethoxy-phenyl)-propylidene]-hydrazino}-phenyl)-5-methyl-4,5-dihydro-2H-pyridazin-3-one The title compound was prepared according to the general method 2

Yield: 71%, melting point 135–140° C. $^1$H NMR (400 MHz, DMSO-d$_6$): δ=1.07 (d, 3H), 2.19–2.23 (m 1H), 2.64–2.67 (m, 1H), 2.77 (t, 2H), 3.15 (t, 2H), 3.31–3.33 (m 1H), 3.69 (s, 3H, OCH$_3$), 3.75 (s, 3H, OCH$_3$), 6.29–6.35 (m, 2H), 6.83–6.87 (m 2H), 6.93 (d, 1H), 7.03 (d, 2H), 7.36 (d, 1H), 7.71 (d, 2H), 9.1 (s, 1H), 9.5 (s, 1H), 10.78 (s, 1H), 12.91 (s, 1H).

Example 15

4-(4-{N'-[(2,4-Dihydroxy-phenyl)-phenyl-methylene]-hydrazino}-phenyl)-2H-phthalazin-1-one The title compound was prepared according to the general method 2.

Yield: 95%, melting point 160–170° C. $^1$H NMR (400 MHz, DMSO-d$_6$): δ=6.7 (m,2 H), 7.3–7.9 (m,13 H), 8.3 (m,1 H), 10.1 (s,1H), 10.7 (s,1H), 12.1 (s,1H), 12.7(s,1H).

Example 16

4-(4-{N'-[(2,4-Dihydroxy-phenyl)-(4-hydroxy-phenyl)-methylene]-hydrazino}-phenyl)-2H-phthalazin-1-one The title compound was prepared according to the general method 2.

Yield: 95%, melting point 150–160° C. $^1$H NMR (400 MHz, DMSO-d$_6$): δ=6.3 (m,2H), 6.8 (m,2 H), 7.4–7.9 (m,10H), 8.3 (m,1H), 10.1 (s,1H), 10.2 (s,1H), 10.4 (s,1H), 12.1 (s,1H), 12.7 (s,1H)

Example 17

4-(4-{N'-[Bis-(2,4-dihydroxy-phenyl)-methylene]-hydrazino}-phenyl)-2H-phthalazin-1-one The title compound was prepared according to the general method 2.

Yield 60%, melting point 140–146° C. $^1$H NMR (400 MHz, DMSO-d$_6$): δ=6.3 (m,4H), 7.1–8.3 (m,10H), 10.1 (s,1H), 10.2 (s,2H), 11.2 (s,2H) 12.7(s,1H).

Example 18

4-{4-[N'-(2,4-Dihydroxy-benzylidene)-hydrazino]-phenyl}-2H-phthalazin-1-one

Yield: 50%, melting point 278–283° C. $^1$H NMR (400 MHz, DMSO-d$_6$): δ=6.3(m,1H), 6.4(m,1H),7,0.4–7,0.9 (m,8H), 8.3(m,1H), 8.9(s,1H), 10.3 (s,1H), 12.8 (s,1H), 13.4 (s,1H).

Example 19

6-{4-[N'-(4-Methanesulfonylbenzylidene)hydrazino]phenyl}-5-methyl-4,5-dihydro-2H-pyridazin-3-one Yield: 54.3%, mp 130–137° C. $^1$H NMR (400 MHz, DMSO-d$_6$): δ=1.08 (d, 3H, CH$_3$), 2.21 (d, 1H, CH), 2.66 (d of d, 1H, CH), 3.22 (s, 3H, CH$_3$), 3.33 (m, 1H, CH), 7.17 (d, 2H, CH), 7.71 (d, 2H, CH), 7.97 (s, 1H, CH), 10.79 (s, 1H, NH), 10.95 (s, 1H, NH).

Example 20

3-{[4-(4-Methyl-6-oxo-1,4,5,6-tetrahydropyridazin-3-yl)phenyl]-hydrazonomethyl}-benzonitrile Yield: 60%, mp 220–224° C. $^1$H NMR (400 MHz, DMSO-d$_6$): δ=1.08 (d, 3H, CH$_3$), 2.22 (d, 1H, CH), 2.66 (d of d, 1H, CH), 3.35 (m, 1H, CH), 7.16 (d, 2H, CH), 7.59 (t, 1H, CH), 7.69 (d, 2H, CH), 7.74 (d, 1H, CH), 7.92 (s, 1H, CH), 8.01 (d, 1H, CH), 8.10 (s, 1H, CH), 10.78 (s, 1H, NH), 10.86 (s, 1H, NH).

Example 21

6-{4-[N'-(2,4-Dihydroxybenzylidene)hydrazino]phenyl}-5-methyl-2H-pyridazin-3-one The product was recrystallized from dimethylformamide.

Yield: 55%, mp 303–310° C. $^1$H NMR (400 MHz, DMSO-d$_6$): δ=2.16 (s, 3H, CH$_3$), 6.35 (m, 2H, CH), 6.79 (s, 1H, CH), 6.97 (d, 2H, CH), 7.34 (m, 3H, CH), 8.10 (s, 1H, CH), 9.69 (s, 1H, OH), 10.33 (s, 1H, NH), 10.63 (s, 1H, OH), 12.90 (s, 1H, NH).

Example 22

6-{4-[N'-(4-Hydroxy-3-methoxy-2-nitrobenzylidene)hydrazino]phenyl}-5-methyl-2H-pyridazin-3-one Yield: 71.0%, mp 264–268° C. $^1$H NMR (400 MHz, DMSO-d$_6$): δ=2.15 (s, 3H, CH$_3$), 3.85 (s, 3H, OCH$_3$), 6.79 (s, 1H, CH), 7.01 (d, 2H, CH), 7.09 (d, 1H, CH), 7.33 (d, 2H, CH), 7.38 (d, 1H, CH), 7.68 (s, 1H, CH), 10.62 (s, 1H, NH), 10.65 (s, 1H, OH), 12.91 (s, 1H, NH).

Example 23

6-{4-{N'-[1-(2,4-Dihydroxyphenyl)ethylidene]hydrazino}phenyl}-5-methyl-2H-pyridazin-3-one The title compound was prepared according to the general method 2. The product was refluxed in propionitrile with acetic acid as a catalyst.

Yield: 32%, mp 299–303° C. $^1$H NMR (400 MHz, DMSO-$d_6$): δ=2.16 (d, 3H, CH$_3$), 2.35 (s, 3H, CH$_3$), 6.28 (d, 1H, CH), 6.33 (d of d, 1H, CH), 6.79 (d, 1H, CH), 7.07 (d, 2H, CH), 7.38 (d, 1H, CH), 7.39 (d, 2H, CH), 9.50 (s, 1H, NH), 9.69 (s, 1H, OH), 12.92 (s, 1H, OH), 12.97 (s, 1H, NH).

Example 24

6-{4-[N'-(2,4-Dihydroxybenzylidene)hydrazino]phenyl}-2,5-dimethyl-2H-pyridazin-3-one Yield: 82%, mp 266–269° C. $^1$H NMR (400 MHz, DMSO-$d_6$): δ=2.16 (d, 3H, CH$_3$), 3.66 (s, 3H, CH$_3$), 6.32 (d, 1H, CH), 6.34 (d of d, 1H, CH), 6.84 (d, 1H, CH), 6.97 (d, 2H, CH), 7.32 (d, 1H, CH), 7.36 (d, 2H, CH), 8.10 (s, 1H, CH), 9.69 (s, 1H), 10.36 (s, 1H), 10.61 (s, 1H).

Example 25

6-{4-[N'-(2,4-Dihydroxybenzylidene)hydrazino]phenyl}-2-methyl-2H-pyridazin-3-one Yield: 82.4%, mp 304–306° C. $^1$H NMR (400 MHz, DMSO-$d_6$): δ=3.72 (s, 3H, CH$_3$), 6.36 (m, 2H, CH), 6.99 (m, 3H, CH), 7.36 (d, 1H, CH), 7.76 (d, 2H, CH), 7.96 (d, 1H, CH), 8.12 (s, 1H, CH), 9.72 (s, 1H), 10.44 (s, 1H), 10.57 (s, 1H).

Example 26

6-{4-{N'-[1-(2,4-dihydroxyphenyl)ethylidene]hydrazino}phenyl}-2-methyl-2H-pyridazin-3-one A solution of 6-(4-hydrazinophenyl)-2-methyl-2H-pyridazin-3-one (0.78 g) and 2,4-dihydroxy-acetophenone (0.55 g) in acetonitrile (20.0 ml) was heated under reflux for 5 hrs. Chrystals formed at room temperature were filtered away. On cooling the filtrate overnight the product chrystallized out. This was filtered, washed with warm ethanol and dried under reduced pressure. Yield: 5.6%, mp 263–268° C.

$^1$H NMR (400 MHz, DMSO-$d_6$): δ=2.35 (s, 3H, CH$_3$), 3.72 (s, 3H, CH$_3$), 6.30 (s, 1H, CH), 6.34 (d, 1H, CH), 6.99 (d, 1H, CH), 7.09 (d, 2H, CH), 7.39 (d, 1H, CH), 7.82 (d, 2H, CH), 7.99 (d, 1H, CH), 9.58 (s, 1H, NH), 9.71 (s, 1H, OH), 12.90 (s, 1H, OH).

Example 27

6-{4-{N'-[1-(2,4-Dihydroxyphenyl)propylidene]hydrazino}phenyl}-2-methyl-2H-pyridazin-3-one The title compound was prepared according to the general method 2.

Yield: 29%, mp 225–233° C. $^1$H NMR (400 MHz, DMSO-$d_6$): δ=1.15 (t, 3H, CH$_3$), 2.87 (q, 2H, CH$_2$), 3.73 (s, 3H, CH$_3$), 6.33 (d, 1H, CH), 6.37 (d of d, 1H, CH), 6.99 (d, 1H, CH) 7.13 (d, 2H, CH), 7.37 (d, 1H, CH), 7.82 (d, 1H, CH), 7.99 (d, 1H, CH), 9.67 (s, 1H), 9.73 (s, 1H), 12.98 (s, 1H).

Example 28

6-{4-[N'-(2,4-Dihydroxy-3-ethylbenzylidene)hydrazino]phenyl}-2-methyl-2H-pyridazin-3-one Yield: 37%, mp 262–266° C. $^1$H NMR (400 MHz, DMSO-$d_6$): δ=1.08 (t, 3H, CH$_3$), 2.61 (q, 2H, CH$_2$), 3.71 (s, 3H, CH$_3$), 6.43 (d, 1H, CH), 6.96 (d, 2H, CH), 6.99 (d, 1H, CH), 7.01 (d, 1H, CH), 7.79 (d, 2H, CH), 7.96 (d, 1H, CH), 8.05 (s, 1H, CH), 9.67 (s, 1H), 10.49 (s, 1H), 11.30 (s, 1H).

Example 29

4-(2,4-Dihydroxyphenyl)-4-{[4-(1-methyl-6-oxo-1,6-dihydropyridazin-3-yl)phenyl]hydrazono}butyric acid The title compound was prepared according to the general method 2.

Yield: 15.9%, mp 138–141° C. $^1$H NMR (400 MHz, DMSO-$d_6$): δ=2.51 (t, 2H, CH$_2$), 3.06 (t, 2H, CH$_2$), 3.72 (s, 3H, CH$_3$), 6.30 (s, 1H, CH), 6.34 (d, 1H, CH), 7.01 (d, 1H, CH), 7.10 (d, 2H, CH), 7.32 (d, 1H, CH), 7.83 (d, 2H, CH), 7.01 (d, 1H, CH), 9.72 (s, 1H), 9.78 (s, 1H), 12.31 (s, 1H), 12.74 (s, 1H).

Example 30 (Intermediate)

6-(4-hydrazinophenyl)-5-methyl-2H-pyridazin-3-one

The title compound was prepared from 6-(4-aminophenyl)-5-methyl-2H-pyridazin-3-one similarly as 6-(4-hydrazinophenyl)-5-methyl-4,5-dihydro-2H-pyridazin-3-one.

$^1$H NMR (400 MHz, DMSO-$d_6$): δ=2.13 (s, 3H, CH$_3$), 4.11 (s, 2H, NH$_2$), 6.75 (s, 1H, CH), 6.81 (d, 2H, CH), 6.95 (s, 1H, NH), 7.21 (d, 2H, CH), 12.82 (s, 1H, NH).

Example 31 (Intermediate)

6-(4-hydrazinophenyl)-2,5-dimethyl-2H-pyridazin-3-one

The title compound was prepared from 6-(4-aminophenyl)-2,5-dimethyl-2H-pyridazin-3-one similarly as 6-(4-hydrazinophenyl)-5-methyl-4,5-dihydro-2H-pyridazin-3-one.

$^1$H NMR (400 MHz, DMSO-$d_6$): δ=2.14 (d, 3H, CH$_3$), 3.63 (s, 3H, CH$_3$), 4.12 (s, 2H, NH$_2$), 6.81 (d, 2H, CH), 6.82 (d, 1H, CH), 6.98 (s, 1H, NH), 7.22 (d, 2H, CH).

Example 32 (Intermediate)

6-(4-hydrazinophenyl)-2-methyl-2H-pyridazin-3-one

The title compound was prepared from 6-(4-aminophenyl)-2-methyl-2H-pyridazin-3-one similarly as 6-(4-hydrazinophenyl)-5-methyl-4,5-dihydro-2H-pyridazin-3-one.

$^1$H NMR (400 MHz, DMSO-$d_6$): δ=3.69 (s, 3H, CH$_3$), 4.18 (s, 2H, NH$_2$), 6.83 (d, 2H, CH), 6.94 (d, 1H, CH), 7.11 (s, 1H, NH), 7.65 (d, 2H, CH), 7.93 (d, 1H, CH).

Example 33

6-(4-{N'-[1-(2,4-Dihydroxy-phenyl)-ethylidene]-hydrazino}-phenyl)-5-methyl-4,5-dihydro-2H-pyridazin-3-one The title compound was prepared according to the general method 2.

Yield 74%, Melting point: 259–261° C. $^1$H NMR (DMSO-$d_6$): δ=1.07 (d, 3H), 2.21 (d, 1H), 2.35 (s, 3H), 2.63–2.68 (m, 1H), 3.30–3.36 (m, 1H), 6.28 (d, 1H), 6.34 (q, 1H), 7.03 (d, 2H), 7.37 (d, 1H), 7.71 (d, 2H), 9.57 (s, 1H), 9.70 (s, 1H), 10.78 (s, 1H), 12.91 (s 1H).

Example 34

6-(4-{N'-[Bis-(2,4-dihydroxy-phenyl)-methylene]-hydrazino}-phenyl)-5-methyl-4,5-dihydro-2H-pyridazin-3-one The title compound was prepared according to the general method 2.

Yield 13%, Melting point: 150–>175° C. $^1$H NMR (DMSO-d$_6$): δ=1.06 (d, 3H), 2.19 (d, 1H), 2.61–2.67 (m, 1H), 3.30–3.36 (m, 1H), 6.16–6.19 (q, 1H), 6.03 (d, 1H), 6.37–6.39 (q, 1H), 6.47 (d, 1H), 6.55 (d, 1H), 6.84 (d, 1H), 7.02 (d, 2H), 7.66 (d, 2H), 8.93 (broad, 1H), 9.72 (broad, 3H), 10.76 (s, 1H), 12.71 (s 1H).

Example 35

6-(4-{N'-[1-(2,5-Dihydroxy-phenyl)-ethylidene]-hydrazino}-phenyl)-5-methyl-4,5-dihydro-2H-pyridazin-3-one The title compound was prepared according to the general method 2.

Yield 73%, Melting point: 279–284° C. $^1$H NMR (DMSO-d$_6$): δ=1.08 (d, 3H), 2.21 (d, 1H), 2.34 (s, 3H), 2.63–2.69 (m, 1H), 3.32–3.38 (m, 1H), 6.66–6.73 (m, 2H), 6.93 (s, 1H), 7.09 (d, 2H), 7.73 (d, 2H), 8.85 (s, 1H), 9.73 (s, 1H), 10.80 (s, 1H), 11.85 (s, 1H).

Example 36

6-{4-[N'-(2,4-Dihydroxy-benzylidene)-hydrazino]-phenyl}-5-ethyl-4,5-dihydro-2H-pyridazin-3-one Yield 29%, Melting point: 270–275° C. $^1$H NMR (DMSO-d$_6$): δ=0.87 (t, 3H), 1.38–1.54 (m, 2H), 2.36 (d, 1H), 2.56–2.62 (q, 1H), 3.12–3.38 (m, 1H), 6.32 (m, 2H), 6.93 (d, 2H), 7.33 (d, 1H), 7.67 (d, 2H), 8,08 (s, 1H), 9.68 (s, 1H), 10.34 (s, 1H), 10.55 (s, 1H), 10.71 (s, 1H).

Example 37

N-[4-(1-{[4-(4-Methyl-6-oxo-1,4,5,6-tetrahydro-pyridazin-3-yl)-phenyl]-hydrazono}-ethyl)-phenyl]-acetamide The title compound was prepared according to the general method 2.

Yield 41%, Melting point: 145–155° C. $^1$H NMR (DMSO-d$_6$): δ=1.07 (d, 3H), 2.05 (s, 3H), 2.23 (d, 1H), 2.24 (s, 3H), 2.61–2.68 (m, 1H), 3.30–3.36 (m, 1H), 7.24 (d, 2H), 7.60 (d, 2H), 7.67 (d, 2H), 7.74 (d, 2H), 9.45 (s, 1H), 10.01 (s, 1H), 10.75 (s, 1H).

Example 38

6-(4-{N'-[1-(2,4-Dihydroxy-3-methyl-phenyl)-ethylidene]-hydrazino}-phenyl)-5-methyl-4,5-dihydro-2H-pyridazin-3-one Yield 47%, Melting point: 244–248° C. $^1$H NMR (DMSO-d$_6$): δ=1.07 (d, 3H), 2.03 (s, 3H), 2.20 (d, 1H), 2.63–2.68 (m, 1H), 3.30–3.36 (m, 1H), 6.43 (d, 1H), 6.91 (d, 2H), 7.01 (d, 1H), 7.70 (d, 2H), 8.05 (s, 1H), 9.69 (s, 1H), 10.46 (s, 1H), 10.76 (s, 1H), 11.31 (s, 1H)

Example 39

6-{4-[N'-(3-Acetyl-2,4-dihydroxy-benzylidene)-hydrazino]-phenyl}-5-methyl-4,5-dihydro-2H-pyridazin-3-one Yield 72%, Melting point: 268–270° C. $^1$H NMR (DMSO-d$_6$): δ=1.07 (d, 3H), 2.20 (d, 1H), 2.61–2.66 (m, 1H), 2.69 (s, 3H), 3.30–3.36 (m, 1H), 6.53 (d, 1H), 6.98 (d, 2H), 7.70 (m, 3H), 8.15 (s, 1H), 10.56 (s, 1H), 10.76 (s, 1H), 11.89 (s, 1H), 13.91 (s, 1H)

Example 40

6-{4-[N'-(3-Ethyl-2,4-dihydroxy-benzylidene)-hydrazino]-phenyl}-5-methyl-4,5-dihydro-2H-pyridazin-3-one Yield 36%, Melting point: 238–240° C. $^1$H NMR (DMSO-d$_6$): δ=1.05–1.09 (m, 3H, 3H), 2.21 (d, 1H), 2.60–2.64 (m, 3H), 3.30–3.36 (m, 1H), 6.42 (d, 1H), 6.90 (d, 2H), 7.00 (d, 1H), 7.71 (d, 2H), 8.04 (s, 1H), 9.65 (s, 1H), 10.46 (s, 1H), 10.76 (s, 1H), 11.31 (s, 1H).

Example 41

N-(3-Hydroxy-4-{[4-(4-methyl-6-oxo-1,4,5,6-tetrahydro-pyridazin-3-yl)-phenyl]-hydrazonomethyl}-phenyl)-acetamide Yield 39%, Melting point: 269–275° C. $^1$H NMR (DMSO-d$_6$): δ=1.07 (d, 3H), 2.03 (s, 3H), 2.20 (d, 1H), 2.61–2.67 (m, 1H), 3.28–3.34 (m, 1H), 6.97–7.01 (m, 3H), 7.36 (d, 1H), 7.49 (d, 1H), 7.68 (d, 2H), 8.12 (s, 1H), 9.96 (s, 1H), 10.42 (s, 1H), 10.52 (s, 1H), 10.75 (s, 1H).

Example 42

6-{4-[N'-(2,4-Dichloro-benzylidene)-hydrazino]-phenyl}-5-methyl-4,5-dihydro-2H-pyridazin-3-one Yield 53%, Melting point: 252–254° C. $^1$H NMR (DMSO-d$_6$): δ=1.07 (d, 3H), 2.21 (d, 1H), 2.63–2.68 (m, 1H), 3.28–3.37 (m, 1H), 7.13 (d, 2H), 7.45 (q, 1H), 7.64 (d, 1H), 7.70 (d, 2H), 8.04 (d, 1H), 8.19 (s, 1H), 10.78 (s, 1H), 11.02 (s, 1H)

Example 43

6-{4-[N'-(2,4-Dihydroxy-3-propyl-benzylidene)-hydrazino]-phenyl}-5-methyl-4,5-dihydro-2H-pyridazin-3-one Yield 61%, Melting point: 160–170° C. $^1$H NMR (DMSO-d$_6$): δ=0.92 (t, 3H), 1.07 (d, 3H), 1.48–1.53 (m,2H), 2.21 (d, 1H), 2.55–2.58 (m, 2H), 2.62–2.68 (m, 1H), 3.30–3.35 (m, 1H), 6.42 (d, 1H), 6.91 (d, 2H), 7.00 (d, 1H), 7.70 (d, 2H), 8.04 (s, 1H), 9.25 (s, 1H), 10.45 (s, 1H), 10.76 (s, 1H), 11.29 (s, 1H)

Example 44

6-{4-[N'-(3-Butyl-2,4-dihydroxy-benzylidene)-hydrazino]-phenyl}-5-methyl-4,5-dihydro-2H-pyridazin-3-one Yield 74%, Melting point: 218° C. $^1$H NMR (DMSO-d$_6$): δ=0.91 (t, 3H), 1.07 (d, 3H), 1.29–1.38 (m, 2H), 1.45–1.51 (m, 2H), 2.21 (d, 1H), 2.57–2.68 (m, 2H, 1H), 3.29–3.36 (m, 1H), 6.42 (d, 1H), 6.91 (d, 2H), 6.99 (d, 1H), 7.71 (d, 2H), 8.04 (s, 1H), 9.62 (s, 1H), 10.46 (s, 1H), 10.76 (s, 1H), 11.28 (s, 1H).

Example 45 (Intermediate)

6-(3-Hydrazinophenyl)-5-methyl-4,5-dihydro-2H-pyridazin-3-one

The title compound was prepared using method of example 1 starting from 1.5 g of 6-(3-aminophenyl)-5- methyl-4,5-dihydro-2H-pyridazin-3-one (J. Med. Chem. 1974 17(3)). The product was isolated (after addition of sodium hydroxide solution) by extraction to tetrahydrofuran. Crystallisation from acetonitrile yielded 1.0 g of the title compound.

1-HNMR (DMSO-d6, 400 MHz): 1.06 (d, 3H), 2.22 (d, 1H), 2.66 (dd, 1H), 3.30 (m, 1H), 3.97 (s, 2H), 6.78 (s, 1H), 6.81 (m, 1H), 6.98 (m, 1H), 7.14 (t, 1H), 7.23 (t, 1H), 10.86 (s, 1H).

Example 46

6-(3-{N-[Bis(2,4-dihydroxy-phenyl)methylene] hydrazino}phenyl)-5-methyl-4,5-dihydro-2H-pyridazin-3-one A mixture of 6-(3-Hydrazinophenyl)-5-methyl-4,5-dihydro-2H-pyridazin-3-one (0.38 g), 2,2',4,4'-tetrahydroxybenzophenone (0.51 g), acetic acid (0.4 ml), and acetonitrile (7.0 ml) was refluxed for 20 h. Solvents were removed in vacuo and the product was separated using column chromatography (silicagel; toluene, ethyl acetate, acetic acid 8:3:3). Crystallisation from a mixture of ethyl acetate and dichloromethane gave 290 mg of product, mp 195–205° C.

1-HNMR (DMSO-d6, 400 MHz): 1.08 (d, 3H), 2.23 (d, 1H), 2.68 (dd, 1H), 3.31 (m, 1H), 6.17 (dd, 1H), 6,30 (d, 1H), 6.36 (dd, 1H), 6.46 (d 1H), 6,57 (d, 1H), 6.83 (d, 1H), 7.01 (m, 1H), 7.19 (m,1H), 7,28 (t, 1H), 7,45 (t, 1H), 10,92 (s, 1H), 8–14 (broad singlets, 5H).

Example 47

6-{4-[N-(2,4-Dihydroxy-5-nitrobenzylidene) hydrazino]phenyl}-5-methyl-4,5-dihydro-2H-pyridazin-3-one 6-(4-Hydrazinophenyl)-5-methyl-4,5-dihydro-2H-pyridazin-3-one (1.10 g), 2,4-dihydroxy-5-nitrobenzaldehyde (0.92 g) and acetic acid (20 ml) were combined and the resulting mixture was refluxed for 20 min. The mixture was cooled to room temperature and the product filtered, yield 1.95 g, solvated crystals with 1 mol of acetic acid, mp about 290° C. with decomposition.

1-HNMR (DMSO-d6, 400 MHz): 1.08 (d, 3H), 1.91(s, 3H), 2.22 (d, 1H), 2.66 (dd, 1H), 3.36 (m, 1H), 6.58 (s, 1H), 7.03 (d, 2H), 7.70 (d, 2H), 8.11 (s, 1H), 8.34 (s, 1H), 10.69 (s, 1H), 10.76 (s, 1H), 13.04 (s, 1H), 13.58 (s, 1H), 13.95 (s, 1H).

Example 48

6-{4-{N-[4-(Dimethylamino)benzylidene] hydrazino}phenyl}-5-methyl-4,5-dihydro-2H-pyridazin-3-one 6-(4-Hydrazinophenyl)-5-methyl-4,5-dihydro-2H-pyridazin-3-one (1.1 g), 4-(dimethylamino)benzaldehyde (0.83 g), acetic acid (0,60 ml) and acetonitrile (15 ml) were combined and the resulting mixture was heated to boil, cooled to room temperature and the product was filtered and washed with acetonitrile, yield 1.50 g, mp 225–232° C.

1-HNMR (DMSO-d6, 400 MHz): 1.07 (d, 3H), 2.21 (d, 1H), 2.64 (dd, 1H), 2.94 (s, 6H), 3.34 (m, 1H), 6.73 (d, 2H), 7.04 (d, 2H), 7.49 (d, 2H), 7.65 (d, 2H), 7.81 (s, 1H), 10.24 (s, 1H), 10.73 (s, 1H).

Example 49

6-(4-{N-[1-(2,4-Dihydroxy-3-methylphenyl) ethylidene]hydrazino}phenyl)-5-methyl-4,5-dihydro-2H-pyridazin-3-one The title compound was prepared according to the general method 2.

Yield 41%, m.p. 268–271° C. 1-HNMR (DMSO-d6, 400 MHz): 1.07 (d, 3H), 2.20 (d, 1H), 2.65 (dd, 1H), 3.35 (m, 1H), 6.40 (d, 1H), 7.05 (d, 2H), 7.24 (d, 1H), 7.73 (d, 2H), 9.55 (s, 1H), 9.57 (s, 1H), 10.77 (s, 1H), 13.25 (s, 1H).

Example 50

6-{4-[N-(2,4-Dimethoxybenzylidene)hydrazino] phenyl}-5-methyl-4,5-dihydro-2H-pyridazin-3-one Yield 90%, m.p. 215–218° C. 1-HNMR (DMSO-d6, 400 MHz): 1.07 (d, 3H), 2.17 (d, 1H), 2.63 (dd, 1H), 3.31 (m, 1H), 3.80 (s, 3H), 3.84 (s, 3H), 6.58–6.61 (m, 2H), 7.03 (d, 2H), 7.65 (d, 2H), 7.78 (d, 1H), 8.16 (s, 1H), 10.43 (s, 1H), 10.73 (s, 1H).

Example 51

6-{4-[N-(2-Hydroxy-4-methoxybenzylidene) hydrazino]phenyl}-5-methyl-4,5-dihydro-2H-pyridazin-3-one Yield 93%, m.p. 214–216° C. 1-HNMR (DMSO-d6, 400 MHz): 1.07 (d, 3H), 2.20 (d, 1H), 2.64 (dd, 1H), 3.34 (m, 1H), 3.75 (s, 3H), 6.46–6.51 (m, 2H), 6.96 (d, 2H), 7.47 (d, 1H), 7.68 (d, 2H), 8.12 (s, 1H), 10.48 (s, 1H), 10.66 (s, 1H), 10.75 (s, 1H).

Example 52

6-{4-[N'-(4-nitrobenzylidene)-hydrazino]-phenyl}-5-methyl-4,5-dihydro-2H-pyridazin-3-one Yield: 80%, mp 216–217° C. 1H NMR (400 MHz, DMSO-d6): δ=1.08(d,3H), 2.21(d,1H), 2.63–2.66(m,1H), 3.29–3.31(m,1H), 7.19(d,2H), 7.72(d,2H), 7.72 (d,2H), 7.92 (s,1H), 7.99(s,1H), 8.24(d,2H), 10.80(s,1H), 10.10(s,1H)

Example 53

6-{4-[N'-(2-Methoxy-benzylidene)-hydrazino]-phenyl}-5-methyl-4,5-dihydro-2H-pyridazin-3-one Yield: 78%, mp 180–183° C. 1H NMR (400 MHz, DMSO-d6): δ=1.07(d,3H), 2.20(d,1H), 2.62–2.67(m,1H), 3.32–3.34(m,1H), 3.85(s,3H), 6.97–7.00(m,1H), 7.06(d, 2H), 7.29–7.32(m, 1H), 7.66 (d,2H), 7.87(d,1H), 8.25(s,1H), 10.61(s,1H), 10.75(s,1H)

Example 54

6-{4-[N'-(2-Hydroxy-benzylidene)-hydrazino]-phenyl}-5-methyl-4,5-dihydro-2H-pyridazin-3-one Yield: 90%, mp 265–268° C. 1H NMR (400 MHz, DMSO-d6): δ=1.07(d,3H), 2.20(d,1H), 2.62–2.68(m,1H), 3.32–3.36(m,1H), 6.86–6.90(m,1H), 7.01(d,2H), 7.16–7.20 (m, 1H), 7.60 (d,2H), 7.69(d,1H), 8.20(s,1H), 10.37(s,1H), 10.64(s,1H), 10.76(s,1H)

Example 55

6-{4-[N'-(4-Methoxy-benzylidene)-hydrazino]-phenyl}-5-methyl-4,5-dihydro-2H-pyridazin-3-one Yield: 82%, mp 172–174° C. 1H NMR (400 MHz, DMSO-d6): δ=1.08(d,3H), 2.19(d,1H), 2.61–2.67(m,1H), 3.29–3.31(m,1H), 3.79(s,3H), 6.98(d,2H), 7.07(d,2H), 7.61 (d,2H), 7.66(s,2H), 7.87(s,1H), 10.43(s,1H), 10.75(s,1H)

Example 56

2,6-Dihydroxy-3-{[4-(4-methyl-6-oxo-1,4,5,6-tetrahydro-pyridazin-3-yl)-phenyl]-hydrazonomethyl}-benzoic acid Yield: 51%, mp 215–218° C. 1H NMR (400 MHz, DMSO-d6): δ=1.06(d,3H), 2.20(d,1H), 2.61–2.67(m,1H), 3.30–3.36(m,1H), 6.24(d,1H), 6.99(d,2H), 7.63(d,2H), 7.65 (d,1H), 8.16(s,1H), 10.00(s, 1H), 10.71(s, 1H), 10.90(s,1H)

Example 57

6-{4-[N'-(2-Hydroxy-3-methoxy-benzylidene)-hydrazino]-phenyl}-5-methyl-4,5-dihydro-2H-pyridazin-3-one Yield: 93%, mp 210–213° C. 1H NMR (400 MHz, DMSO-d6): δ=1.08(d,3H), 2.20(d,1H), 2.62–2.67(m,1H), 3.35–3.39(m,1H), 3.81(s,1H) 6.82(t,1H), 6.93(d,1H), 7.02 (d,2H), 7.22(d,1H), 7.69(d,2H), 8.21(s,1H), 9.88(s,1H), 10.64(s,1H), 10.77(s,1H)

Example 58

6-{4-[N'-(2-nitro-benzylidene)-hydrazino]-phenyl}-5-methyl-4,5-dihydro-2H-pyridazin-3-one Yield: 77%, mp 250–253° C. 1H NMR (400 MHz, DMSO-d6): δ=1.07(d,3H), 2.20(d,1H), 2.63–2.70(m,1H), 3.29–3.36(m,1H), 7.14(d,2H), 7.50–7.54(m,1H), 7.70(d, 2H), 7.71–7.75(m,1H), 7.99(d,1H), 8.17(s,1H), 8.30(s,1H), 10.79(s,1H), 11.11(s,1H)

Example 59

6-{4-[N'-(2,6-Dinitro-benzylidene)-hydrazino]-phenyl}-5-methyl-4,5-dihydro-2H-pyridazin-3-one Yield: 20%, mp 216–218° C. 1H NMR (400 MHz, DMSO-d6): δ=1.06(d,3H), 2.20(d,1H), 2.63–2.70(m,1H), 3.29–3.36(m,1H), 6.96(d,2H), 7.68–7.74(m,3H), 8.11 (s,1H), 8.22(d,2H), 10.81(s,1H), 11.29(s,1H)

Example 60

4-{[4-(4-Methyl-6-oxo-1,4,5,6-tetrahydro-pyridazin-3-yl)-phenyl]-hydrazonomethyl}-benzonitrile Yield: 85%, mp 246–248° C. 1H NMR (400 MHz, DMSO-d6): δ=1.07(d,3H), 2.21(d,1H), 2.63–2.67(m,1H), 3.30–3.35(m,1H), 7.16(d,2H), 7.70(d,2H), 7.82 (d,2H), 7.84 (d,2H), 7.93(d,2H), 10.79(s,1H), 10.97(s,1H)

Example 61

6-{4-[N'-(4-Hydroxy-benzylidene)-hydrazino]-phenyl}-5-methyl-4,5-dihydro-2H-pyridazin-3-one Yield: 86%, mp 258–261° C. 1H NMR (400 MHz, DMSO-d6): δ=1.07(d,3H), 2.19(d,1H), 2.61–2.67(m,1H), 3.30–3.35(m,1H), 6.79(d,2H), 7.04(d,2H), 7.48 (d,2H), 7.65 (d,2H), 7.82(s,1H), 966(s,1H), 10.33(s,1H), 10.73(s,1H)

Example 62

6-{4-[N'-(3-Hydroxy-benzylidene)-hydrazino]-phenyl}-5-methyl-4,5-dihydro-2H-pyridazin-3-one Yield: 80%, mp 267–270° C. 1H NMR (400 MHz, DMSO-d6): δ=1.07(d,3H), 2.20(d,1H), 2.61–2.67(m,1H), 3.33–3.36(m,1H), 6.71–6.73(dd,1H), 7.04–7.12(m,4H), 7.18–7.21(m,1H), 7.68(d,2H), 7.82(s,1H), 9.46(s,1H), 10.54 (s,1H), 10.76(s,1H)

Example 63

6-{4-[N'-(4-Hydroxy-3-nitro-benzylidene)-hydrazino]-phenyl}-5-methyl-4,5-dihydro-2H-pyridazin-3-one Yield: 21%, mp 230–233° C. 1H NMR (400 MHz, DMSO-d6): δ=1.07(d,3H), 2.19(d,1H), 2.62–2.69(m,1H), 3.31–3.36(m,1H), 7.09(d,2H), 7.16(d,1H), 7.67(d,2H), 7.88 (s,1H), 7.89–7.91(dd,1H), 8.11(d,1H), 10.64(s,1H), 10.76(s, 1H), 11.00(s,1H)

Example 64

4-(2,4-Dihydroxy-phenyl)-4-{[4-(4-methyl-6-oxo-1,4,5,6-tetrahydro-pyridazin-3-yl)-phenyl]-hydrazono}-butyric acid Yield: 26%, mp 299–302° C. 1H NMR (400 MHz, DMSO-d6): δ=1.07(d,3H), 2.19(d,1H), 2.49–2.51(t,2H), 2.64–2.67(m,1H), 3.03–3.05(t,2H), 3.28–3.31(m,1H), 6.29 (d,1H), 6.33–6.35(dd,1H), 7.04(d,2H), 7.32(d,1H), 7.72(d, 2H), 9.71(s,1H), 9.79(s,1H), 10.78(s,1H), 12.00(s,1H), 12.77(s,1H)

Example 65

6-{4-[N'-(2,4-Dinitro-benzylidene)-hydrazino]-phenyl}-5-methyl-4,5-dihydro-2H-pyridazin-3-one Yield: 50%, mp 278–280° C. 1H NMR (400 MHz, DMSO-d6): δ=1.07(d,3H), 2.21(d,1H), 2.64–2.70(m,1H), 3.37–3.40(m,1H), 7.22(d,2H), 7.75(d,2H), 8.37(s,1H), 8.43 (d,1H), 8.44(d,1H), 8.74(d,1H), 10.84(s,1H), 11.62(s,1H)

Example 66

5-(2,4-Dihydroxy-phenyl)-5-{[4-(4-methyl-6-oxo-1,4,5,6-tetrahydro-pyridazin-3-yl)-phenyl]-hydrazono}-pentanoic acid Yield: 39%, mp 235–240° C. 1H NMR (400 MHz, DMSO-d6): δ=1.04–1.08(m,5H), 1.72–1.74(m,2H), 2.22(d, 1H), 2.64–2.67(m,1H), 2.80–2.82(m,2H), 3.30–3.36(m,1H), 6.29(d,1H), 6.32–6.35(dd,1H), 7.04(d,2H), 7.41(d,1H), 7.72 (d,2H), 9.77(s,1H), 9.71(s,1H), 10.78(s,1H), 12.00(s,1H), 12.88(s,1H)

Example 67

6-(4-{N'-[1-(4-Hydroxy-3-methoxy-2-nitro-phenyl)-ethylidene]-hydrazino}-phenyl)-5-methyl-4,5-dihydro-2H-pyridazin-3-one Yield: 46%, mp 251–254° C. 1H NMR (400 MHz, DMSO-d6): δ=1.06(d,3H), 2.19(d,1H), 2.21(s,3H), 2.61–2.65(m,1H), 3.30–3.36(m,1H), 3.83(s,3H), 7.06(d, 2H), 7.08(d,2H), 7.28(d,2H), 7.63(d,1H), 9.49(s,1H), 10.55 (s,1H), 10.75(s,1H)

What is claimed is:

1. A compound of formula (I):

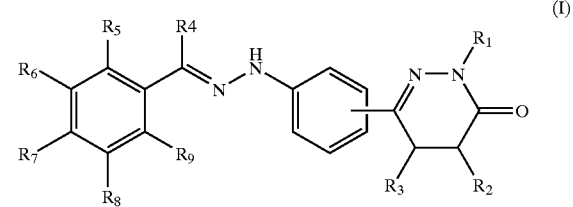

(I)

in which

R$_1$ to R$_3$ are independently hydrogen, alkyl, alkenyl, aryl, arylalkyl, carboxyalkyl, hydroxyalkyl or halogenalkyl, or R$_2$ and R$_3$ form a ring of 5–7 carbon atoms, R$_4$ is hydrogen, alkyl, alkenyl, substituted aryl, arylalkyl, carboxyalkyl, hydroxyalkyl or halocienalkyl, $R_5$ to $R_9$ are independently hydrogen, alkyl, alkenyl, aryl, arylalkyl, acyl, hydroxy, alkoxy, alkoxycarbonyl, amino, acylamino, alkylamino, aryloxy, halogen, cyano, nitro, carboxy, alkylsulfonyl, sufonamido or trifluoromethyl, wherein each aryl residue defined above by itself or as a part of another group may be substituted, or a pharmaceutically acceptable salt thereof, provided that a) when $R_1$, $R_2$, $R_3$, $R_5$, $R_6$, $R_8$ and $R_9$ are hydrogen and $R_4$ is methyl, $R_7$ is not hydrogen, methoxy, cyano or methyl and b) when $R_1$, $R_2$, $R_3$, $R_5$, $R_6$, $R_7$ and $R_8$ are hydrogen and $R_4$ is methyl, $R_9$ is not hydroxy or chloro and c) when $R_1$, $R_2$, $R_3$, $R_5$, $R_6$, $R_7$ and $R_9$ are hydrogen and $R_4$ is methyl, $R_8$ is not trifluoromethyl.

2. A compound of claim 1 wherein $R_5$ to $R_9$ are independently hydrogen, $C_{1-6}$alkyl, $C_{2-6}$alkenyl $C_{6-10}$aryl, $C_{7-12}$arylalkyl, $C_{1-6}$acyl, hydroxy, $C_{1-6}$alkoxy, $C_{1-6}$alkoxycarbonyl, amino, $C_{1-6}$acylamino, $C_{1-6}$alkylamino, $C_{6-10}$aryloxy, halogen, cyano, nitro, carboxy, $C_{1-6}$alkylsulfonyl, sulfonamido or trifluoromethyl.

3. A compound of claim 2 wherein $R_5$ to $R_9$ are independently hydrogen, hydroxy, $C_{1-6}$alkyl, $C_{1-6}$alkoxy, carboxy, $C_{1-6}$alkoxycarbonyl or nitro.

4. A compound of claim 3 wherein $R_5$ is hydroxy, $C_{1-6}$alkyl, $C_{1-6}$alkoxy, carboxy, $C_{1-6}$alkoxycarbonyl or nitro.

5. A compound of claim 4 wherein $R_5$ is hydroxy or nitro.

6. A compound of claim 1 wherein $R_1$ to $R_3$ are independently hydrogen, $C_{1-6}$alkyl, $C_{2-6}$alkenyl $C_{6-10}$aryl, $C_{7-12}$arylalkyl, $C_{1-6}$carboxyalkyl, $C_{1-6}$hydroxyalkyl or $C_{1-6}$halogenalkyl, or $R_2$ and $R_3$ form a phenyl ring, and $R_4$ is hydrogen, $C_{1-6}$alkyl, $C_{2-6}$alkenyl, substituted $C_{6-10}$aryl, $C_{7-12}$arylalkyl, $C_{1-6}$carboxyalkyl, $C_{1-6}$hydroxyalkyl or $C_{1-6}$halogenalkyl.

7. A compound of claim 1 wherein $R_1$ to $R_3$ are independently hydrogen or $C_{1-6}$alkyl.

8. A pharmaceutical composition comprising a compound of formula (I):

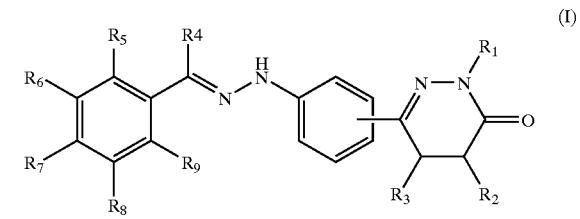

(I)

in which $R_1$, $R_2$, $R_3$, $R_5$, $R_6$, $R_8$ and $R_9$ are hydrogen, $R_4$ is methyl and $R_7$ is hydrogen, methoxy, cyano or methyl, or in which $R_1$, $R_2$, $R_3$, $R_5$, $R_6$, $R_7$ and $R_8$ are hydrogen, $R_4$ is methyl and $R_9$ is hydroxy or chloro or in which $R_1$, $R_2$, $R_3$, $R_5$, $R_6$, $R_7$ and $R_9$ are hydrogen, $R_4$ is methyl and $R_8$ is trifluoromethyl, or a pharmaceutically acceptable salt thereof, together with a pharmaceutically acceptable carrier.

9. A pharmaceutical composition comprising a compound of claim 1 as an active ingredient together with a pharmaceutically acceptable carrier.

10. A method for the treatment of congestive heart failure comprising administering to a subject in need thereof a therapeutically effective amount of a compound of claim 1.

11. A method for the treatment of congestive heart failure comprising administering to a subject in need thereof a therapeutically effective amount of a pharmaceutical composition as claimed in claim 8.

* * * * *

UNITED STATES PATENT AND TRADEMARK OFFICE
CERTIFICATE OF CORRECTION

PATENT NO. : 6,699,868 B2
DATED : March 2, 2004
INVENTOR(S) : Jarmo Pystynen et al.

It is certified that error appears in the above-identified patent and that said Letters Patent is hereby corrected as shown below:

Title page,
Item [57], ABSTRACT, in formula (I), "R4" should read -- $R_4$ --.; "alkylsufonyl," should read -- alkylsulfonyl, --.

Column 18,
Lines 52-60, in formula (I), "R4" should read -- $R_4$ --.
Line 67, "halocienalkyl," should read -- halogenalkyl, --.

Column 19,
Line 4, "sufonamido" should read -- sulfonamido --.

Column 20,
Lines 4-12, in formula (I), "R4" should read -- $R_4$ --.

Signed and Sealed this

Twelfth Day of October, 2004

JON W. DUDAS
*Director of the United States Patent and Trademark Office*